US007655914B2

(12) United States Patent
Musrock et al.

(10) Patent No.: US 7,655,914 B2
(45) Date of Patent: Feb. 2, 2010

(54) METHOD AND APPARATUS FOR DETERMINING TIMING INFORMATION IN POSITRON EMISSION TOMOGRAPHY (PET) DETECTION

(75) Inventors: Mark Musrock, Oak Ridge, TN (US); Michael E. Casey, Louisville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 13 days.

(21) Appl. No.: 11/772,934

(22) Filed: Jul. 3, 2007

(65) Prior Publication Data

US 2009/0008563 A1    Jan. 8, 2009

(51) Int. Cl.
*G01T 1/164* (2006.01)
(52) U.S. Cl. .............................. 250/363.04; 250/363.03

(58) Field of Classification Search ............ 250/363.04, 250/363.03
See application file for complete search history.

(56) References Cited

U.S. PATENT DOCUMENTS

| 3,141,144 | A | * | 7/1964 | Watts, Jr. ..................... 333/161 |
| 4,583,049 | A | * | 4/1986 | Powell ....................... 330/151 |
| 5,567,944 | A | * | 10/1996 | Rohe et al. ............. 250/370.09 |
| 5,841,140 | A | * | 11/1998 | Mc Croskey et al. ... 250/363.03 |
| 2005/0211893 | A1 | * | 9/2005 | Paschalidis ................. 250/287 |

* cited by examiner

*Primary Examiner*—David P Porta
*Assistant Examiner*—Mark R Gaworecki

(57) ABSTRACT

A constant fraction discriminating circuit outputs timing information corresponding to an event corresponding to a detected photon for providing nuclear medicine imaging. The constant fraction discriminating circuit includes a stripline or microstrip delay element.

6 Claims, 6 Drawing Sheets

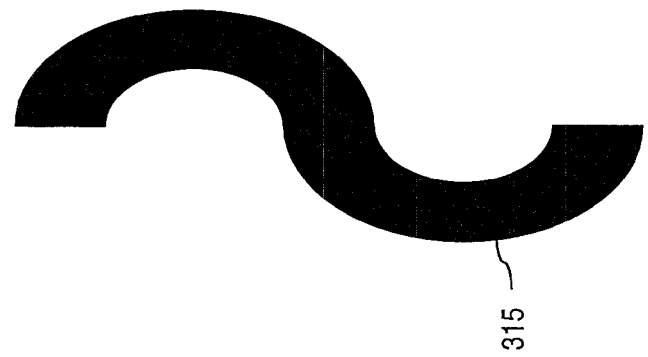
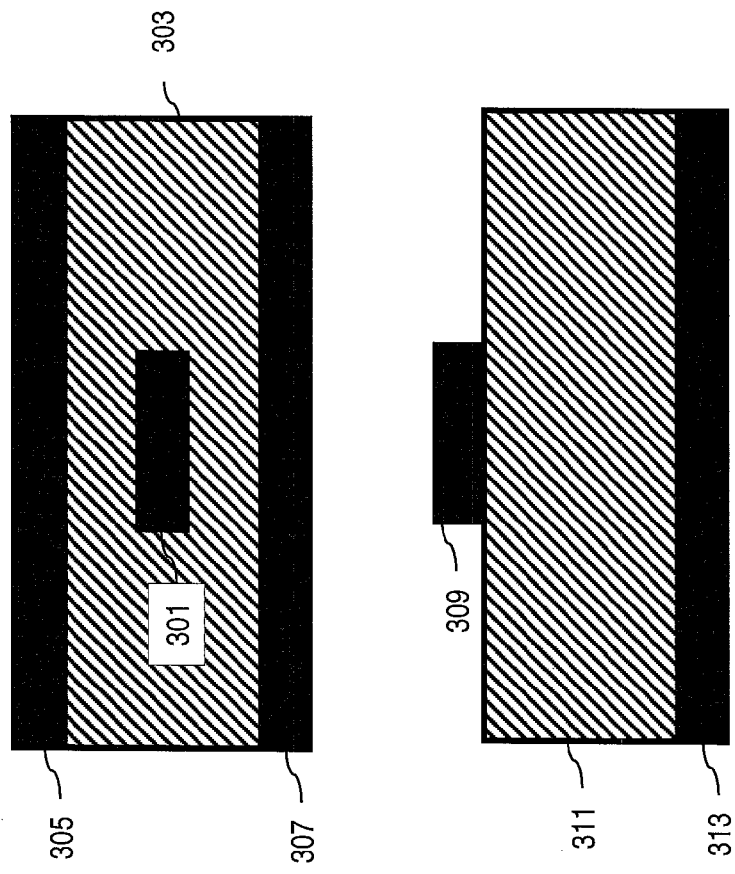
FIG. 3A   FIG. 3B   FIG. 3C

METHOD AND APPARATUS FOR DETERMINING TIMING INFORMATION IN POSITRON EMISSION TOMOGRAPHY (PET) DETECTION

FIELD OF THE INVENTION

The present invention, according to certain embodiments, relates to nuclear medicine imaging.

BACKGROUND OF THE INVENTION

Medical radionuclide imaging, commonly referred to as nuclear medicine, is a significant diagnostic tool that involves the use of ionizing radiation to obtain accurate imaging of an in vivo patient. Typically, one or more biologically appropriate radiopharmaceuticals are administered to a patient, as by ingestion, inhalation, or injection. Tracer amounts of these radioactive substances emanate gamma quanta while localizing at specific organs, bones, or tissues of interest within the patient's body. One or more radiation detectors (e.g., positron emission tomography (PET) detector) are then used to record the internal spatial distribution of the radiopharmaceutical as it propagates from the study area. Known applications of nuclear medicine include: analysis of kidney function, imaging blood-flow and heart function, scanning lungs for respiratory performance, identification of gallbladder blockage, bone evaluation, determining the presence and/or spread of cancer, identification of bowel bleeding, evaluating brain activity, locating the presence of infection, and measuring thyroid function and activity. Hence, accurate detection is vital in such medical applications.

For accurate detection, the acquisition of timing information is critical. PET detectors rely on Constant Fraction Discriminators (CFDs) to provide accurate time determination of the arrival of an incident photon to the detector. Conventionally, CFD circuitry utilizes co-axial cables for the delay elements to allow for the necessary adjustment to obtain amplitude invariant timing for a wide range in possible detector risetimes. The use of co-axial cables and corresponding connectors introduce rather significant costs to the CFD circuitry.

Based on the foregoing, there is a clear need for an improved detector for nuclear medicine imaging.

DISCLOSURE OF THE INVENTION

According to certain embodiments, a detector is provided that introduces an electronic Constant Fraction Discriminator (CFD) timing channel using a printed circuit board stripline or microstrip for the delay element with sufficient timing accuracy to be used in a time of flight positron emission tomography (PET) scanner.

Additional advantages of the present invention will become readily apparent to those skilled in the art from the following detailed description, wherein embodiments of the present invention are described, simply by way of illustration of the best mode contemplated for carrying out the present invention. As will be realized, the present invention is capable of other and different embodiments and its several details are capable of modifications in various obvious respects, all without departing from the present invention.

BRIEF DESCRIPTION OF THE DRAWINGS

Various exemplary embodiments are illustrated by way of example, and not by way of limitation, in the figures of the accompanying drawings in which like reference numerals refer to similar elements and in which:

FIGS. 3A-3C are diagrams of exemplary configurations of the delay element in the detector of FIG. 2, according to an exemplary embodiment;

DESCRIPTION OF THE PREFERRED EMBODIMENTS

A method and apparatus for providing depth-of-interaction detection using position emission tomography (PET) are described. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Figure 1:
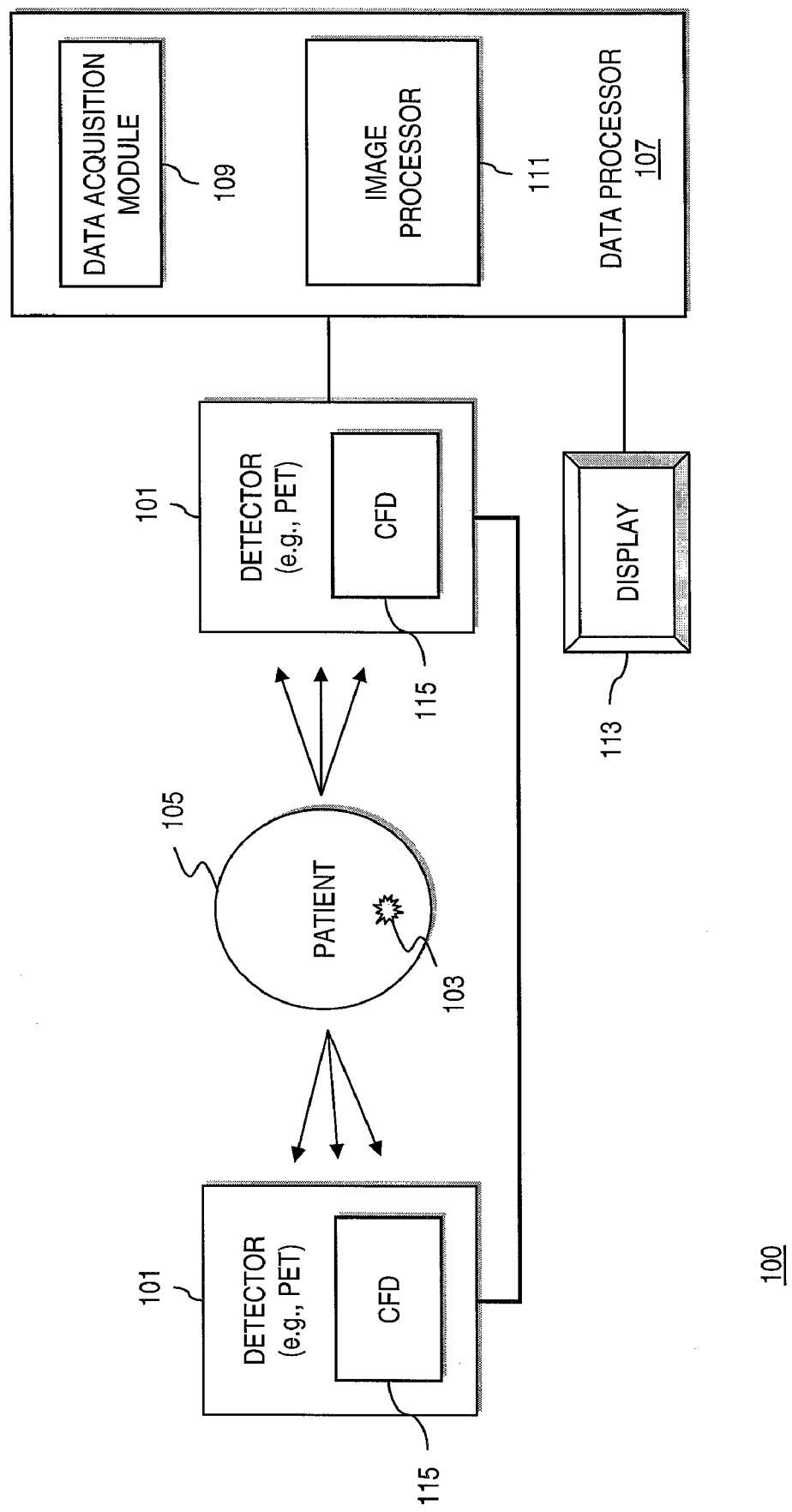
FIG. 1 is a diagram of a detection system utilizing a positron emission tomography (PET) detection, according to various embodiments.

FIG. 1 is a diagram of a detection system utilizing a positron emission tomography (PET) detection, according to various embodiments. As shown, a detection system 100 includes a detectors 101 to observe events stemming from a radiation source 103 emitting radiation (e.g., gamma rays) from a subject (patient) 105. The detectors 101 output data to a data processor 107, which includes a data acquisition module 109 and an image processor 111. The data acquisition module 109 uses spatial coordinate signals to produce input to the image processor 111. The image processor 111 can then produce, for example, an image of tissues in the patient 105. The image can then be displayed on a display unit 113.

In positron emission tomography (PET), it is necessary to detect the timing of each detected photon as accurately as possible. Consequently, the detector 101 includes a constant fraction discriminator (CFD) 115 to create a timing signal that is ideally independent of both the detected photon's amplitude and risetime. As noted, a key element of the CFD 115 is a delay element which is used to delay the detected electrical signal converted from the photon for later comparison with an attenuated version of the detected photon's electrical signal. This arrangement is further detailed below.

Figure 2:
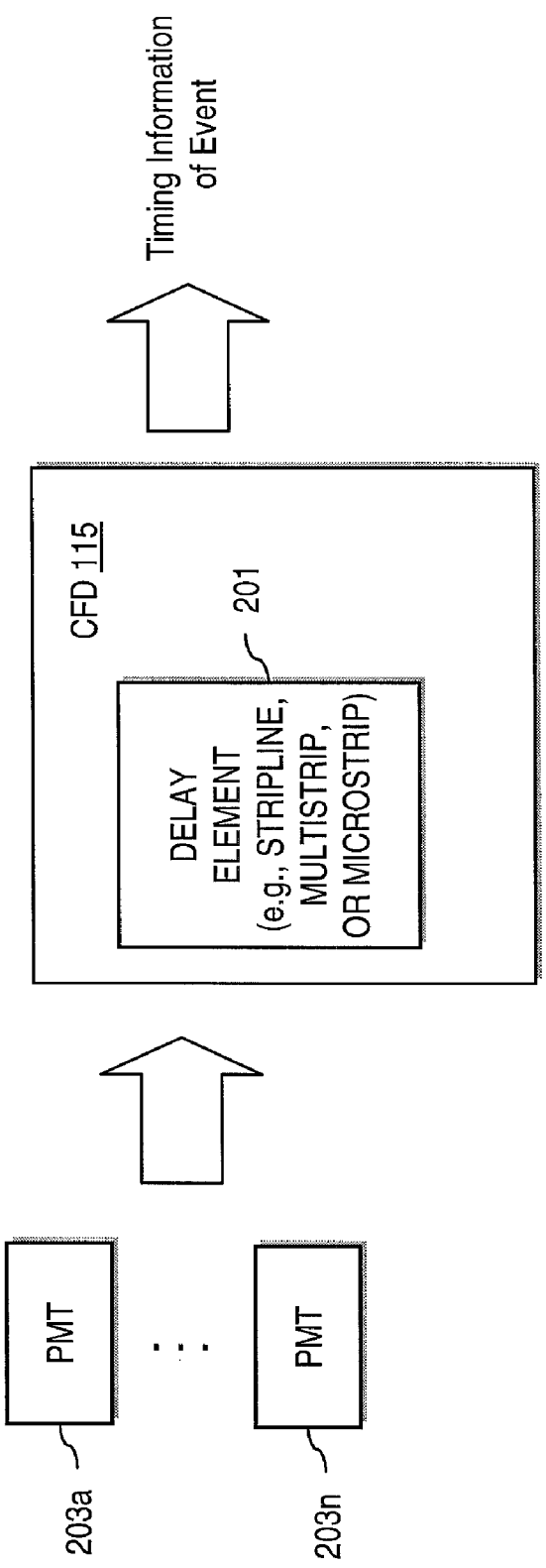
FIG. 2 is a detector used in the system of FIG. 1 employing a constant fraction discriminator (CFD) including a delay element for determining event timing information, according to an exemplary embodiment.

FIG. 2 is a detector used in the system of FIG. 1 employing a constant fraction discriminator (CFD) including a stripline or microstrip delay element for determining event timing information, according to an exemplary embodiment. According to certain embodiments, the CFD 115 uses a printed circuit board stripline or microstrip as the delay element 201. By way of example, the delay element 115 can be used in an electrical circuit to derive the timing signal of a detected photon for a time of flight positron emission tomograph.

In this example, photomultiplier tubes (PMTs) 203a-203n are implemented for time of flight PET scanners. The PMTs 203a-203n exhibit time step responses that permit effective use a microstrip or a stripline on a printed circuit board to realize the delay, since the CFD delay required to produce an amplitude invariant timing signal can be, for example, on the order of one nanosecond or less using high light output scintillation crystals for the detector 101.

Exemplary configurations for the delay element 201 are shown in FIGS. 3A-3C.

FIGS. 3A-3C are diagrams of exemplary configurations of the delay element in the detector of FIG. 2, according to an exemplary embodiment. In FIG. 3A, the delay element 201 is formed on a printed circuit board such that a stripline 301 is surrounded by a dielectric material 303 that is situated between two conductors 305, 307. Additionally, delay element 201 can be a multistrip, which is a single printed circuit board trace over a power plane, while the stripline is a single printed circuit board trace with either symmetric or asymmetric power planes above and below the board trace separated by dielectric.

Alternatively, the delay element 201 is a microstrip 309, as shown in FIG. 3B, formed on a dielectric material 311, which rests atop a conductor 313.

As seen in FIG. 3C, the stripline 301 (or microstrip 309) can have a serpentine configuration or shape 315. It is contemplated that other configurations can be utilized. The serpentine stripline or microstrip 315 has a sufficient area to limit the risetime dispersion of the detector signal so that the overall channel timing resolution is dominated by the scintillation crystal photon statistics.

These arrangements address the concern of using expensive coaxial cable based CFD for the delay element 201. Under this approach, impedance discontinuities can be minimized or reduced at the cable/connector interfaces.

Figure 4:
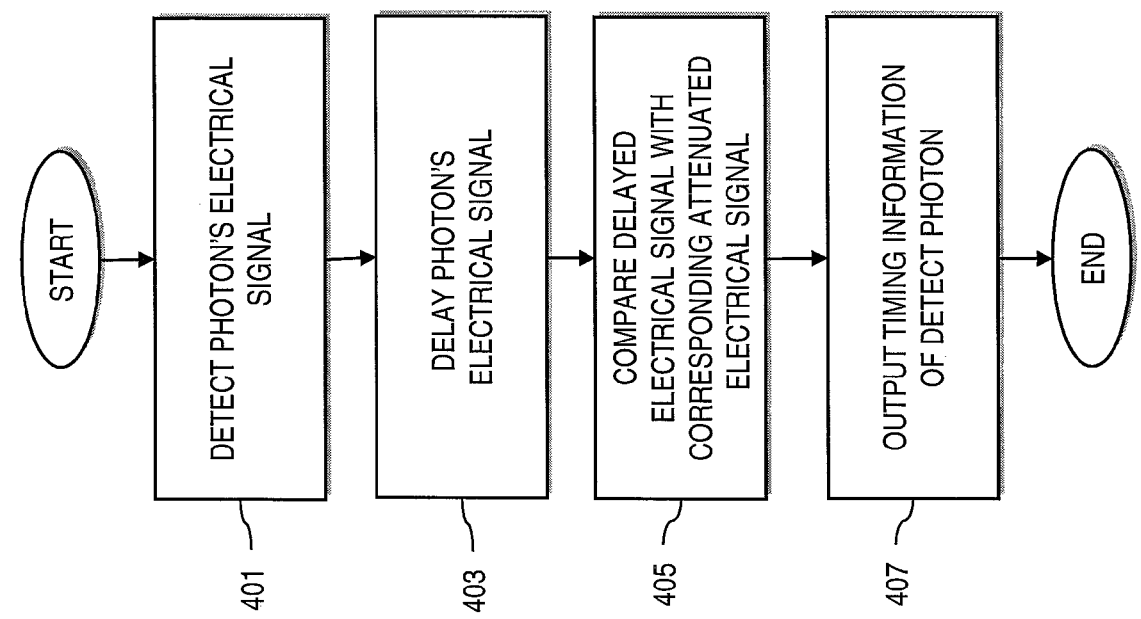
FIG. 4 is a flowchart of a process for determining timing information in PET detection, according to an exemplary embodiment.

FIG. 4 is a flowchart of a process for determining timing information in PET detection, according to an exemplary embodiment. As mentioned, the CFD 115 operates to assist with obtaining timing information. In step 401, an electrical signal corresponding to the detected photon is received. This electrical signal is then delayed using the stripline or microstrip delay element 403, which delays the detected photon's electrical signal. This delayed signal is then used for later comparison with an attenuated version of the detected photon's electrical signal, per step 405. In step 407, the timing information is then output based on this comparison.

Figure 5:
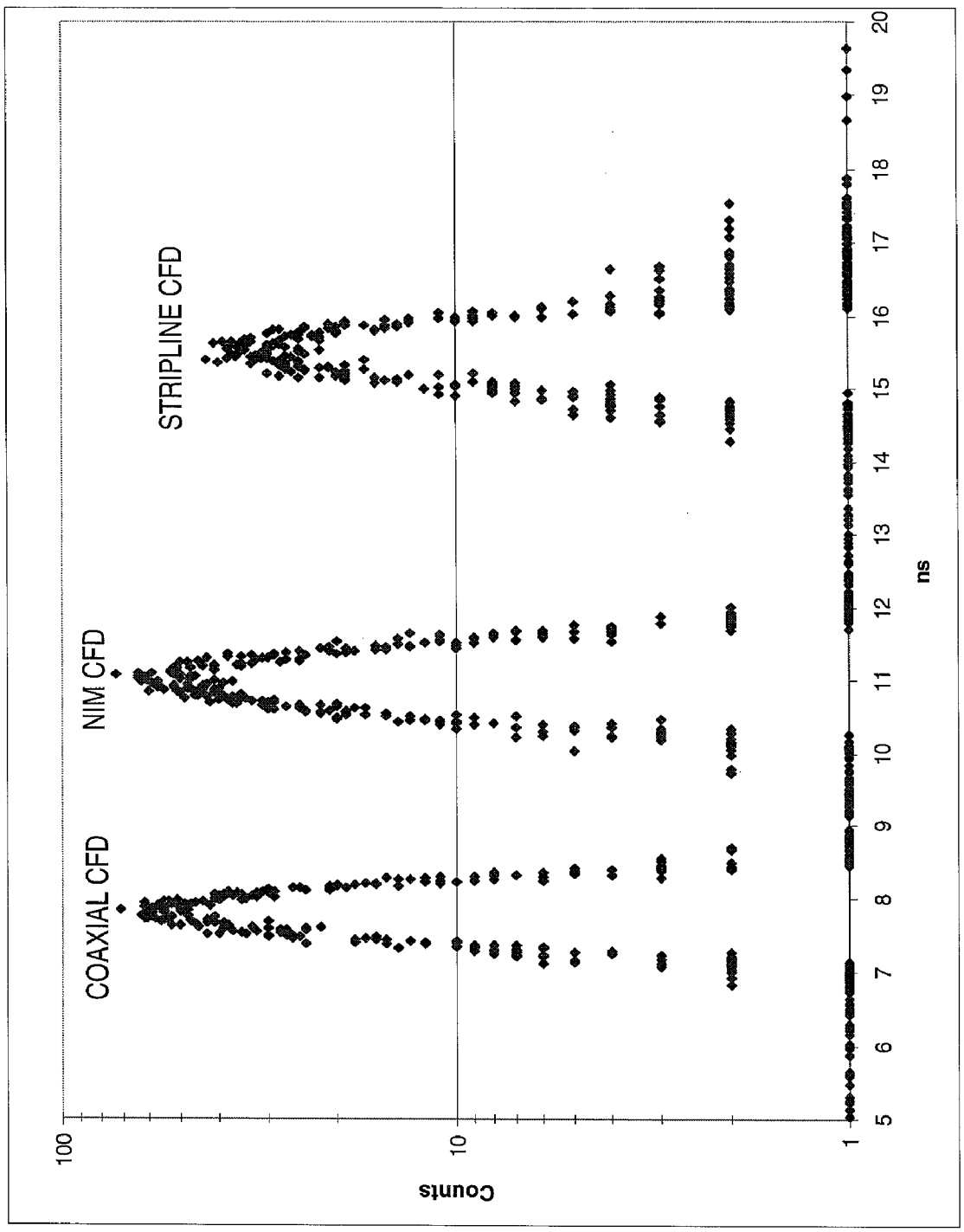
FIG. 5 is a graph showing timing resolution measurement differences between coaxial delay and stripline delay based CFD circuits.

FIG. 5 is a graph showing timing resolution measurement differences between coaxial delay and stripline delay based CFD circuits. Graph 500 shows the timing performance of the stripline based CFD (according to one embodiment) in comparison with a standard coaxial based CFD. The performance of the stripline based CFD showed only a slightly lower performance than a standard coaxial based delay CFD and a state of the art NIM CFD, but at a lower cost.

The data and imaging processes of FIG. 1 may be implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 6:
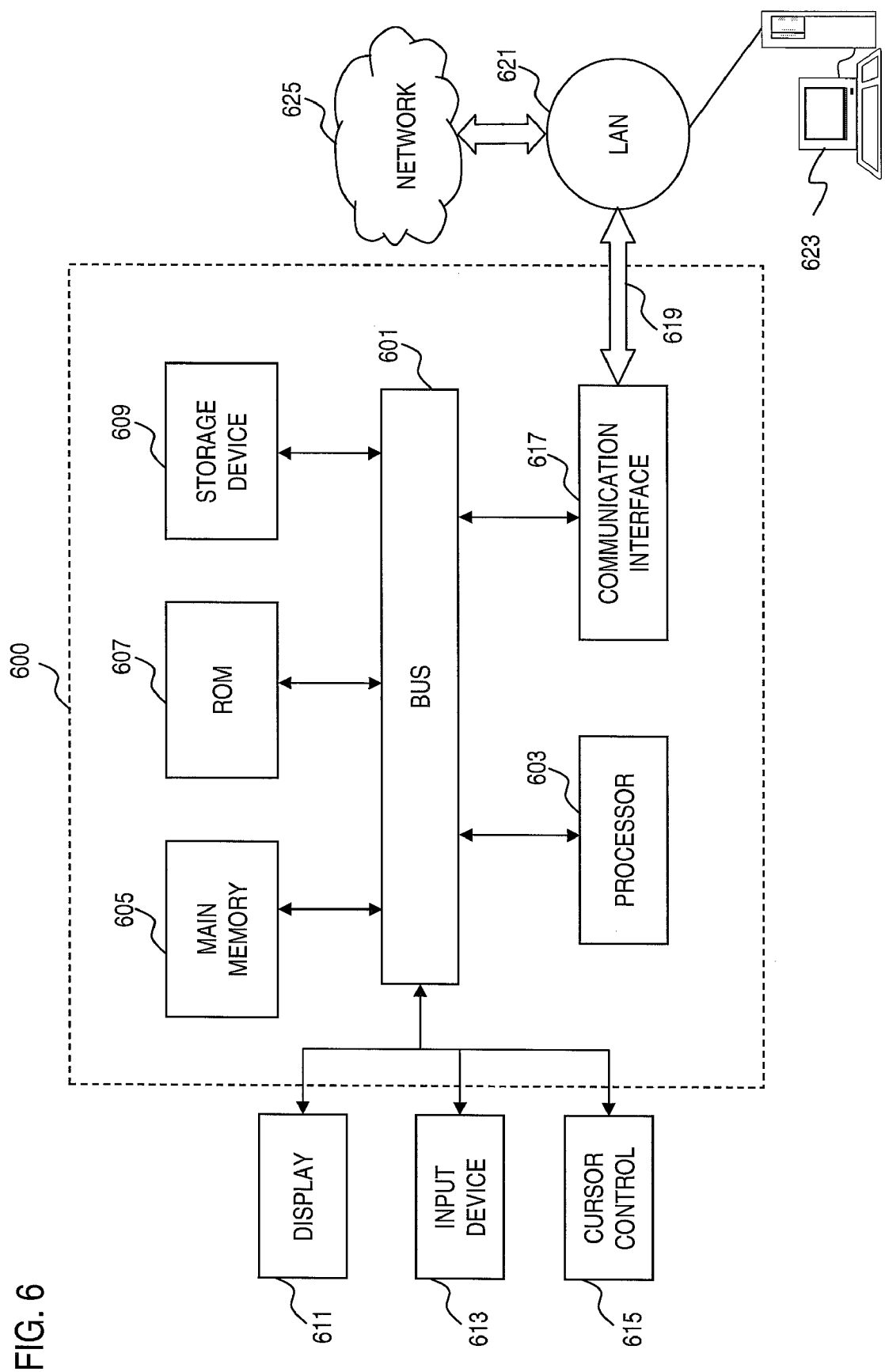
FIG. 6 is a diagram of a computing hardware that can be used to implement various embodiments of the invention.

FIG. 6 illustrates a computing hardware 600 upon which an embodiment according to various exemplary embodiments can be implemented. For example, the processes described herein can be implemented using the computer system 600. The computer system 600 includes a bus 601 or other communication mechanism for communicating information and a processor 603 coupled to the bus 601 for processing information. The computer system 600 also includes main memory 605, such as a random access memory (RAM) or other dynamic storage device, coupled to the bus 601 for storing information and instructions to be executed by the processor 603. Main memory 605 can also be used for storing temporary variables or other intermediate information during execution of instructions by the processor 603. The computer system 600 may further include a read only memory (ROM) 607 or other static storage device coupled to the bus 601 for storing static information and instructions for the processor 603. A storage device 609, such as a magnetic disk or optical disk, is coupled to the bus 601 for persistently storing information and instructions.

The computer system 600 may be coupled via the bus 601 to a display 611, such as a cathode ray tube (CRT), liquid crystal display, active matrix display, or plasma display, for displaying information to a computer user. An input device 613, such as a keyboard including alphanumeric and other keys, is coupled to the bus 601 for communicating information and command selections to the processor 603. Another type of user input device is a cursor control 615, such as a mouse, a trackball, or cursor direction keys, for communicating direction information and command selections to the processor 603 and for controlling cursor movement on the display 611.

According to one embodiment contemplated herein, the processes described are performed by the computer system 600, in response to the processor 603 executing an arrangement of instructions contained in main memory 605. Such instructions can be read into main memory 605 from another computer-readable medium, such as the storage device 609. Execution of the arrangement of instructions contained in main memory 605 causes the processor 603 to perform the process steps described herein. One or more processors in a multi-processing arrangement may also be employed to execute the instructions contained in main memory 605. In alternative embodiments, hard-wired circuitry may be used in place of or in combination with software instructions to implement the certain embodiments. Thus, the exemplary embodiments are not limited to any specific combination of hardware circuitry and software.

The computer system 600 also includes a communication interface 617 coupled to bus 601. The communication interface 617 provides a two-way data communication coupling to a network link 619 connected to a local network 621. For example, the communication interface 617 may be a digital subscriber line (DSL) card or modem, an integrated services digital network (ISDN) card, a cable modem, a telephone modem, or any other communication interface to provide a data communication connection to a corresponding type of communication line. As another example, communication interface 617 may be a local area network (LAN) card (e.g. for Ethernet™ or an Asynchronous Transfer Model (ATM) network) to provide a data communication connection to a compatible LAN. Wireless links can also be implemented. In any such implementation, communication interface 617 sends and receives electrical, electromagnetic, or optical signals that carry digital data streams representing various types of information. Further, the communication interface 617 can include peripheral interface devices, such as a Universal Serial Bus (USB) interface, a PCMCIA (Personal Computer Memory Card International Association) interface, etc. Although a single communication interface 617 is depicted in FIG. 6, multiple communication interfaces can also be employed.

The network link 619 typically provides data communication through one or more networks to other data devices. For example, the network link 619 may provide a connection through local network 621 to a host computer 623, which has connectivity to a network 625 (e.g. a wide area network (WAN) or the global packet data communication network now commonly referred to as the "Internet") or to data equipment operated by a service provider. The local network 621 and the network 625 both use electrical, electromagnetic, or optical signals to convey information and instructions. The signals through the various networks and the signals on the network link 619 and through the communication interface 617, which communicate digital data with the computer system 600, are exemplary forms of carrier waves bearing the information and instructions.

The computer system 600 can send messages and receive data, including program code, through the network(s), the network link 619, and the communication interface 617. In the Internet example, a server (not shown) might transmit requested code belonging to an application program for implementing an exemplary embodiment through the network 625, the local network 621 and the communication interface 617. The processor 603 may execute the transmitted code while being received and/or store the code in the storage device 609, or other non-volatile storage for later execution. In this manner, the computer system 600 may obtain application code in the form of a carrier wave.

The term "computer-readable medium" as used herein refers to any medium that participates in providing instructions to the processor 603 for execution. Such a medium may take many forms, including but not limited to non-volatile media, volatile media, and transmission media. Non-volatile media include, for example, optical or magnetic disks, such as the storage device 609. Volatile media include dynamic memory, such as main memory 605. Transmission media include coaxial cables, copper wire and fiber optics, including the wires that comprise the bus 601. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out various exemplary embodiments may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

While the invention has been described in connection with a number of embodiments and implementations, the invention is not so limited but covers various obvious modifications and equivalent arrangements, which fall within the purview of the appended claims.

What is claimed is:

1. An apparatus comprising:
    a positron emission tomography (PET) detector;
    a constant fraction discriminating circuit configured to output timing information corresponding to an event corresponding to a photon detected by the PET detector for delaying an electrical signal generated by the detected photon for comparison with an attenuated version of the electrical signal;
    wherein the constant fraction discriminating circuit includes a stripline or microstrip delay element having a serpentine form.

2. An apparatus according to claim 1, wherein the delay element is formed in a printed circuit board.

3. A system comprising:
    a positron emission tomography (PET) detector;
    a detector including a constant fraction discriminating circuit configured to output timing information using a stripline or microstrip delay element having a serpentine form; and
    an image processor configured to receive the timing information to compare an electrical signal generated by photon detected by the PET detector with an attenuated version of the electrical signal.

4. A system according to claim 3, wherein the delay element is formed in a printed circuit board.

5. A method comprising:
    receiving an electrical signal generated by a photon detected in a (PET) detector; delaying the electrical signal by a constant fraction discriminating circuit; and
    comparing the delayed electrical signal with an attenuated version of the electrical signal;
    wherein the constant fraction discriminating circuit includes a stripline or microstrip delay element having a serpentine form.

6. A method according to claim 5, wherein the delay element is formed in a printed circuit board.

* * * * *